(12) United States Patent
Karlsson et al.

(10) Patent No.: US 7,459,050 B2
(45) Date of Patent: Dec. 2, 2008

(54) METHOD FOR PRODUCTION OF DIAPER PANTS

(75) Inventors: Birgitta Karlsson, Mölnlycki (SE); Ken Olsson, Västra Frölunda (SE); Cecile Sandin, Mölndal (SE); Elisabeth Lakso, Stenungsund (SE); Anna-Carin Elfström, Torslanda (SE); Robert Albino, Pixbo (SE)

(73) Assignee: SCA Hygiene Products AG, Gothenburg (SE)

( * ) Notice: Subject to any disclaimer, the term of this patent is extended or adjusted under 35 U.S.C. 154(b) by 450 days.

(21) Appl. No.: 10/401,733

(22) Filed: Mar. 31, 2003

(65) Prior Publication Data

US 2003/0212377 A1    Nov. 13, 2003

Related U.S. Application Data

(60) Provisional application No. 60/368,954, filed on Apr. 2, 2002.

(51) Int. Cl.
*A61F 13/15* (2006.01)

(52) U.S. Cl. ........................ 156/204; 156/226

(58) Field of Classification Search ............... 156/226, 156/227; 24/446, 449
See application file for complete search history.

(56) References Cited

U.S. PATENT DOCUMENTS

| 3,387,345 | A | * | 6/1968 | Savoir | .................. | 24/446 |
| 4,940,464 | A | * | 7/1990 | Van Gompel et al. | ....... | 604/396 |
| 6,022,432 | A | | 2/2000 | Elsberg et al. | | |
| 6,036,805 | A | | 3/2000 | McNichols | | |
| 6,113,717 | A | * | 9/2000 | Vogt et al. | .................. | 156/73.1 |
| 6,264,643 | B1 | | 7/2001 | Toyoda | | |
| 2003/0055389 | A1 | * | 3/2003 | Sanders et al. | .............. | 604/358 |

FOREIGN PATENT DOCUMENTS

| DE | 9422298 U1 | 12/1999 |
| EP | 0641552 B2 | 12/1999 |
| WO | 99/65438 A1 | 12/1999 |
| WO | 99/65441 A1 | 12/1999 |
| WO | 00/37007 A1 | 6/2000 |
| WO | 00/37010 A1 | 6/2000 |
| WO | 0035398 A1 | 6/2000 |
| WO | 0037009 A2 | 6/2000 |
| WO | 0187210 A1 | 11/2001 |

* cited by examiner

*Primary Examiner*—Richard Crispino
*Assistant Examiner*—Barbara J. Musser
(74) *Attorney, Agent, or Firm*—Buchanan Ingersoll & Rooney PC

(57) ABSTRACT

A method of production of disposable diaper pants or disposable sanitary panty with openable and resealable side panels. A row of absorption bodies is applied on a continuous web of inner or outer cover sheet material, after which a continuous web of outer or inner cover sheet material is applied and secured to the web with absorption bodies at parts lying outside the absorption bodies to form a web of diaper pants blanks. First side panels having two parts connected by a detachable and resealable connection are secured to the diaper pants blanks at a side of a front or rear portion. Second separate side panels are secured to the side portions of the front or rear portions of the diaper pants blanks which to not have side panels. Individual diaper pants blanks with side panels are cut out, folded along a transverse axis in the crotch, and secured.

9 Claims, 4 Drawing Sheets

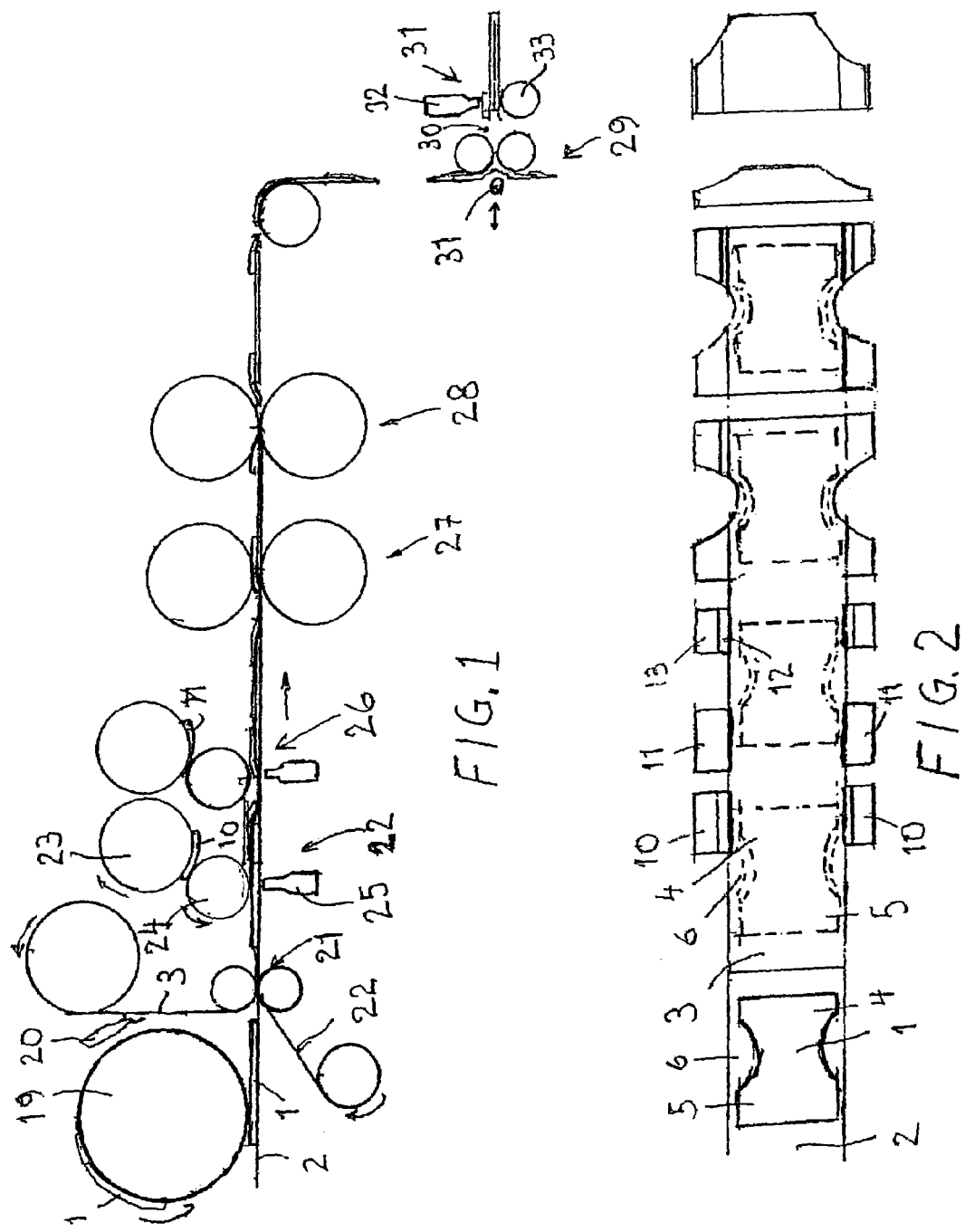

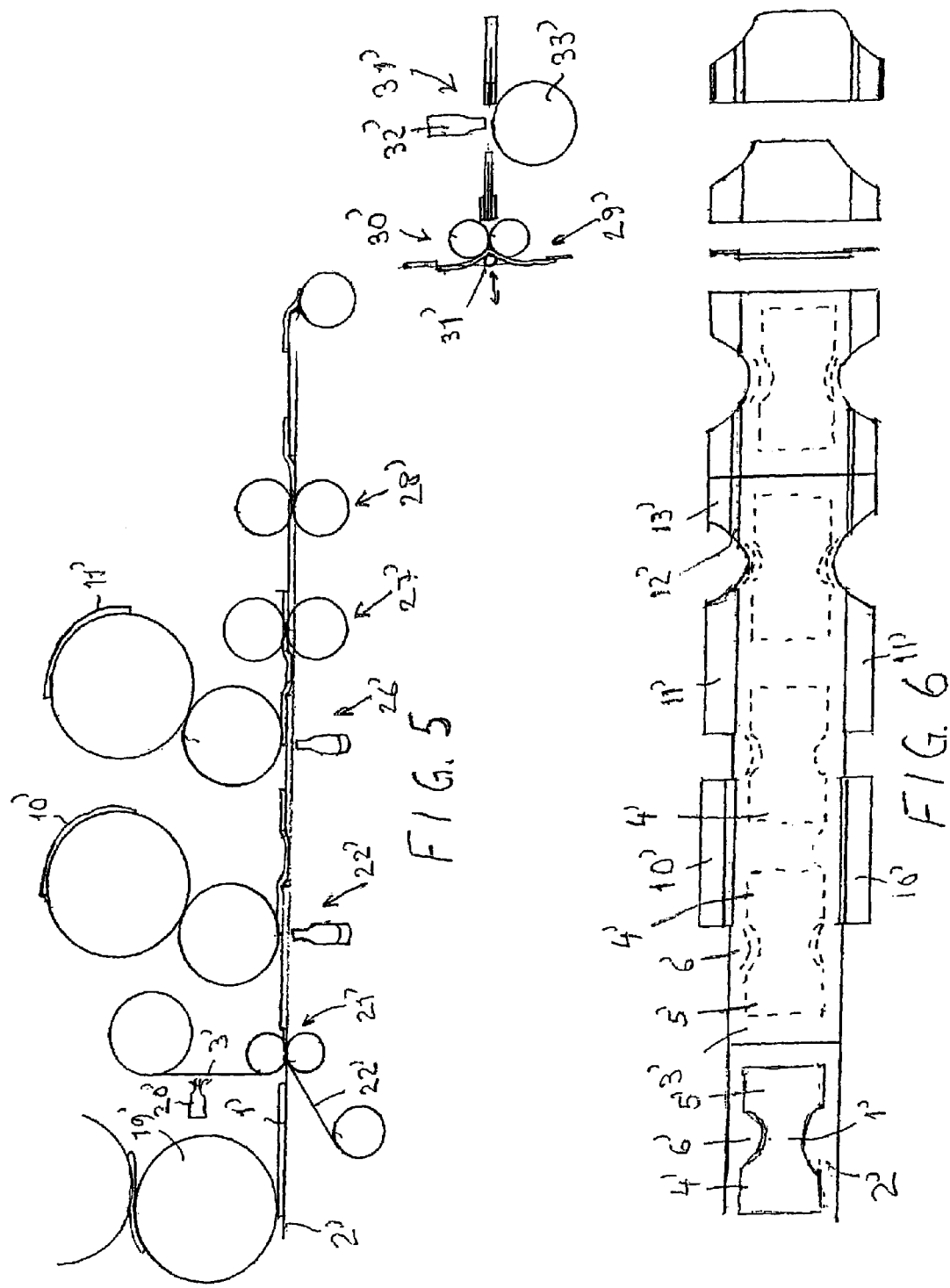

METHOD FOR PRODUCTION OF DIAPER PANTS

CROSS-REFERENCE TO RELATED APPLICATIONS

The present application claims the benefit of U.S. Provisional Application No. 60/368,954, filed in the United States on Apr. 2, 2002, the entire contents of which are hereby incorporated herein by reference.

BACKGROUND OF THE APPLICATION

1. Technical Field

The present invention relates to a method for production of disposable diaper pants or of a sanitary panty of the disposable type with openable and resealable side panels and to disposable diaper pants or a disposable sanitary panty produced by means of this method.

2. Background Art

Diaper pants with openable and resealable side panels combine the advantages of conventional diaper pants and conventional diapers. They are produced with sealed side panels and, like conventional diaper pants, can be taken off and put on in the same way as underpants. By means of the side panels being openable, they can also be taken off in the same way as conventional diapers, as a result of which soiling of the infant can be avoided when changing the diaper pants. Moreover, the fact that they are resealable means that a parent can open the diaper pants in order to check whether they need to be changed and can seal the diaper pants again if this is not the case. It is therefore of advantage to be able to produce such diaper pants in an economic way. WO 99/65439, WO 99/65441, WO 00/37007 and WO 00/37010 all disclose methods for producing diaper pants in which side panels are fastened in a detachable and resealable manner to side portions of the unit of the diaper pants which encloses the absorption body. These methods require great precision when applying the side panels, and they also make it difficult to design the openable and resealable connection as a childproof connection.

It is an object of the present invention to make available a method for production of disposable diaper pants or of a sanitary panty of the disposable type with openable and resealable side panels, the method requiring less precision than in previously known methods for applying side panels to a web of continuous diaper pants blanks arranged in succession. Further objects are to reduce the required precision for cutting individual diaper pants blanks from the web, and to permit application of childproof connections in a simple manner.

SUMMARY OF THE INVENTION

These and other objects are achieved by means of a method for production of disposable diaper pants or of a sanitary panty of the disposable type with openable and resealable side panels, comprising the step in which a web of interconnected diaper pants blanks, which each comprise an absorption body enclosed between an inner cover sheet of liquid-permeable material and an outer cover sheet of liquid-impermeable material and have a front portion and a rear portion and an intermediate crotch portion, is formed by means of a row of absorption bodies being applied on a continuous web of inner or outer cover sheet material, after which a continuous web of outer or inner cover sheet material is applied to the web with absorption bodies and secured to it in those parts thereof which lie outside the absorption bodies. The method includes:

first separate side panels, which each comprise two parts connected to each other by means of a detachable and resealable connection, are secured to the side portions of the front portions or rear portions of the diaper pants blanks;

second separate side panels are secured to the side portions of those of the front portions or rear portions of the diaper pants blanks which are not provided with or are intended to be provided with first side panels; after which individual diaper pants blanks provided with side panels are cut out from the web of interconnected diaper pants blanks; after which each diaper pants blank is folded about a transverse axis in the crotch portion so that the front and rear portions of the blank lie against each other;

after which the first and second side panels of each diaper pants blank which have been folded toward each other are secured to each other.

Because the detachable and resealable connection is made in the two-part front or rear side panel, the detachable and resealable connection can be delivered to the processing line for diaper pants production in the assembled state, which reduces the precision requirements in the processing line compared to the situation where sealing of the connection takes place in the processing line. Moreover, such a design means that the connection can be made childproof outside the processing line, which is advantageous from the point of view of production technology.

In a preferred embodiment, the absorption bodies are arranged such that front and rear portions of the absorption bodies are directed towards each other in adjacent absorption bodies in the row of absorption bodies, and such that the first and second side panels of adjacent diaper pants blanks extend across both the mutually adjacent front and rear portions. The first and second side panels are secured to the outer or inner cover sheet of the diaper pants blanks. Alternatively, the first and second side panels are placed between the outer and inner cover sheet of the diaper pants blanks and secured to both of these sheets. Moreover, the side panels at least partially consist of elastic material, and the detachable and resealable connection, which connects the two parts of each first side panel to each other, preferably consists of a childproof connection.

Embodiments of the invention also relate to disposable diaper pants or a sanitary panty of the disposable type with a front portion, a rear portion and an intermediate crotch portion, which comprises an absorption body enclosed between an inner cover sheet of liquid-permeable material and an outer cover sheet of liquid-tight material and separate side panels which, on both sides of the absorption body, extend outside the inner and outer cover sheets and connect the front and rear portions of the diaper pants to each other, so that the diaper pants acquire a pants-like configuration with a waist opening and two leg openings, which side panels comprise front and rear parts which are connected to each other by a seam. Each side panel is elastic and comprises two parts which are connected to each other by means of a detachable and resealable connection member.

In a preferred embodiment, the detachable and resealable connection consists of a childproof connection member. Alternatively, in addition to the detachable and resealable connection, each side panel also comprises a second childproof connection, which is detachable and is destroyed upon opening the side panel for the first time. The force needed to open a childproof connection is greater than 4 N, preferably greater than 6 N, more preferably greater than 8 N, and most preferably greater than 10 N but less than 20 N, preferably 15 N. Moreover, the elastic side panels comprise parts of non-elastic material in those sections to which parts of the connection members are secured.

BRIEF DESCRIPTION OF THE DRAWINGS

The invention will now be described with reference to the attached figures, of which:

FIGS. 1 and 2 are diagrammatic representations, in a side view and plan view respectively, of an arrangement for producing diaper pants according to a first embodiment of the invention.

DETAILED DESCRIPTION OF THE PREFERRED EMBODIMENTS

Figure 3:
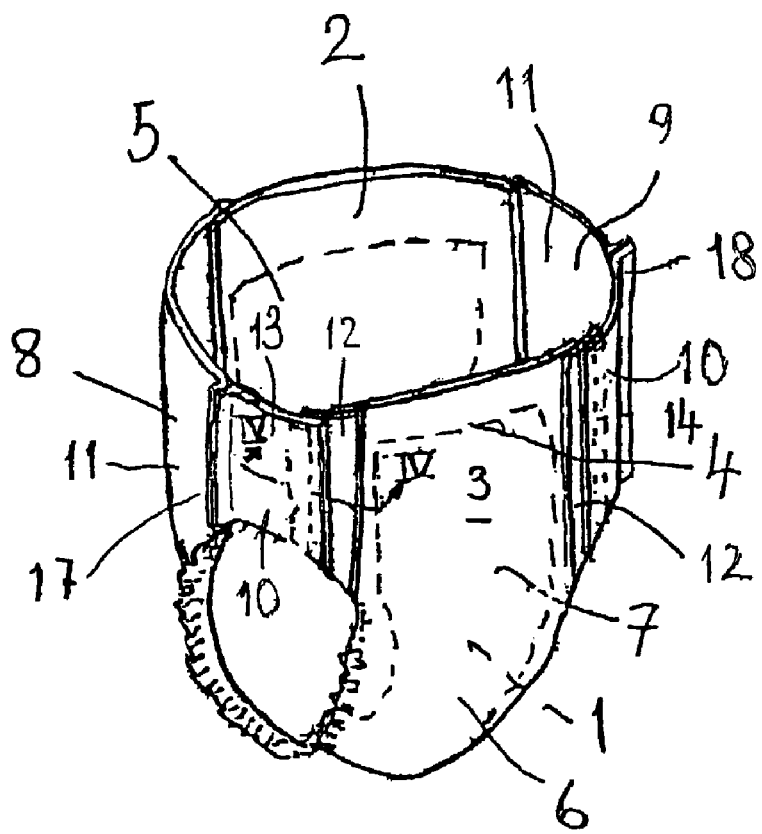
FIG. 3 shows a diagrammatic perspective view of diaper pants produced in an arrangement according to FIGS. 1 and 2.

FIGS. 1 and 2 are diagrammatic representations of an arrangement for producing the diaper pants according to FIG. 3. The diaper pants shown in FIG. 3 comprise an absorption body 1 enclosed between an inner cover sheet 2 of liquid-permeable material and an outer cover sheet 3 of liquid-tight material. The cover sheets 2 and 3 are connected to each other by adhesive bonding or welding in parts lying outside the absorption body. The unit 7 formed by the cover sheets and the absorption body has a front portion 4, a rear portion 5 and an intermediate narrower crotch portion 6. The diaper pants 3 also comprise side panels 8, 9 which extend between the front and rear portions of the unit 7 lying on the same sides of the absorption body and connect these portions to each other so that the diaper pants acquire a form similar to underpants.

Figure 7:
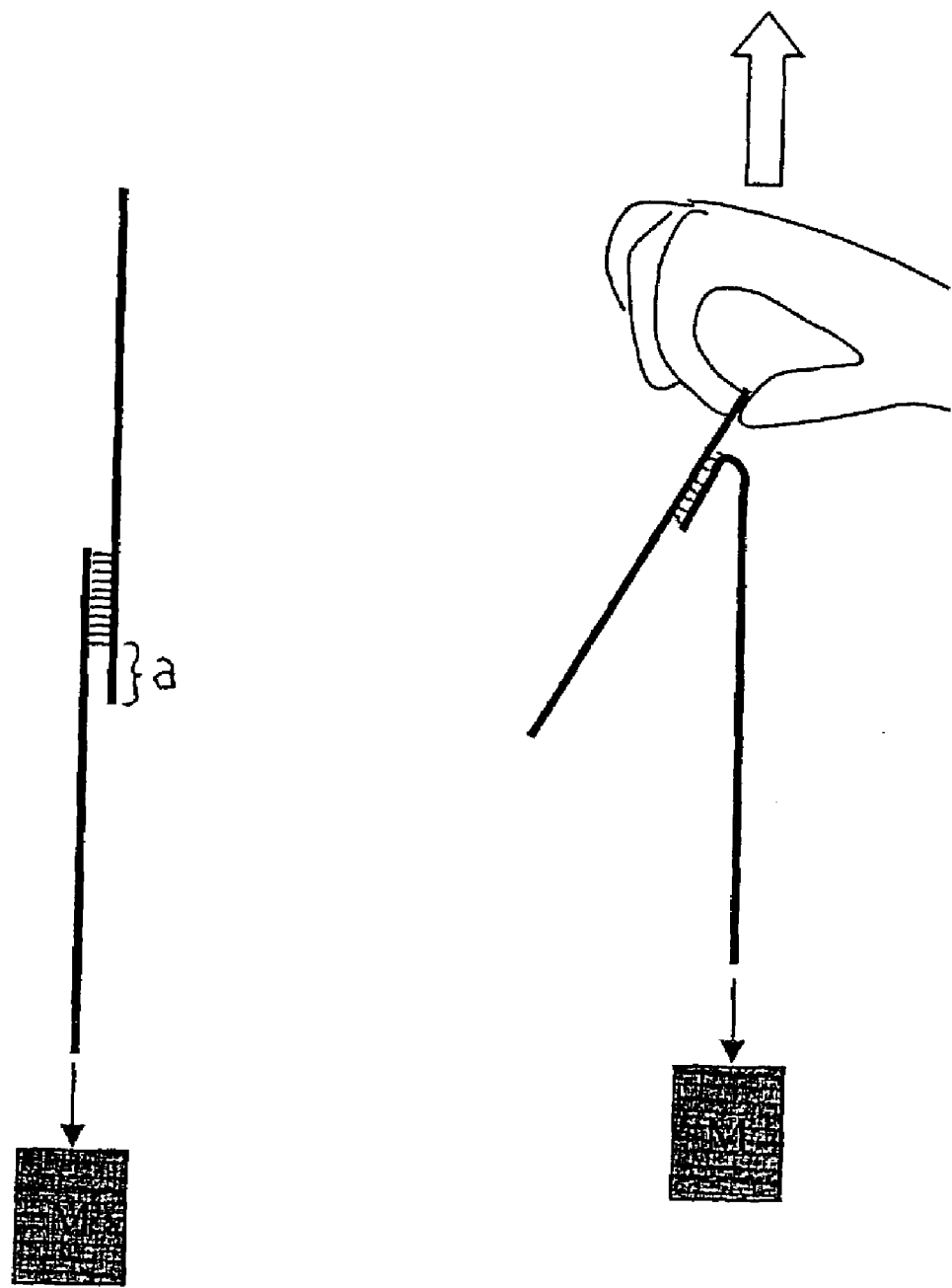
FIG. 7 is a diagrammatic representation of a method for testing the childproof nature of a connection.

The side panels 8, 9 each comprise a front side panel 10 and a rear side panel 11 which are connected to each other by outward seams 17, 18. The seams 17, 18 expediently consist of weld seams but can also be adhesive seams. The front side panels 10 are in turn each made up of two parts 12, 13, which parts are connected to each other by means of a detachable and resealable mechanical connection 14 which, in the example shown, is of the velcro type, i.e. one part 13 is provided with a fastening element 15, or male element, having a number of hooks which project outward from the surface of the fastening element, and the other part 12 is provided with a fastening element 16, or female element, having a number of loops or eyelets in which the hooks engage. In the illustrative embodiment shown, some of the hooks of the male element are also firmly connected to the female element, e.g. firmly welded in the female element by point welding. In this way it is possible to obtain a connection which is difficult or impossible for an infant to open but is easy for an adult to open. It has indeed been found that infants like to manipulate their diaper pants, and for this reason there is a need for a childproof connection. The number of weld points should be chosen so that the force needed to open such a connection is greater than 4 N, preferably greater than 6 N, more preferably greater than 8 N, and most preferably greater than 10 N but less than 20 N, preferably 15 N, in order to ensure childproofing and yet make the connection easy for an adult to open. The opening force can be easily measured, in the manner shown diagrammatically in FIG. 7, by coupling a weight to that part of the two parts of the connection which is overlapped, and thereafter taking hold of the grip part of the overlapping part and then lifting the connection. If the weight remains suspended from the connection for more than 30 seconds without the connection opening, the connection is considered sufficient to hold the weight.

Another factor which influences the childproof aspect is the length of the grip tab, i.e. the length a (see FIG. 7) of that part of the overlapping side panel which projects beyond the connection. It has been found that if the grip tabs are shorter than 7 mm, it is very difficult for the children themselves to open the connection. For this reason, the length of the grip tab should lie between 3 and 7 mm, preferably between 4 and 6 mm.

The childproofing can also be obtained in another way by means of the fact that, outside the mechanical connection 14, the overlapping portions of the two parts 12, 13 of the front side panels are connected to each other by means of a second openable but not resealable connection, for example a weld connection or adhesive connection, with an opening force in accordance with the above. A second connection of this kind is destroyed when the side panels are opened for the first time. The outermost edge part of the overlapping part of the two parts 12, 13 can also be firmly connected to the underlying part of the side panel, in which case opening is obtained by means of a line of weakening in the overlapping part situated between the connection 14 and the firmly connected outermost edge part.

The side panels 8, 9 are elastic and are preferably made of elastic material. However, in those parts which include the securing elements 15, 16, the side panels are preferably made of nonelastic material in order to simplify the attachment of the securing elements. The elastic material can consist of elastics made from block copolymers, such as polyurethanes, copolyether esters, polyamide-polyether block copolymers, ethylene-vinyl acetates (EVA) and the like, including polyurethanes available from E. I. Du Pont de Nemours Co., USA, under the name LYCRA® (also known as "spandex"); elastomeric styrene-butadiene copolymers, including those such as KRATON® material, which are available from Shell Chemical Company of Houston, Tex., USA; tetra-block copolymers, including elastomeric styrene-poly(ethylenepropylene) block copolymers available from Shell Chemical Company of Houston, Tex., USA, under the trade name KRATON®; polyamides including polyether block amides available from Ato Chemical Company, USA, under the trade name PEBAX®;

polyesters, such as those available from E. I. Du Pont de Nemours Co. under the trade name HYTREL®; single-site or metallocene-catalyzed polymers, including single-site or metallocene-catalyzed polyolefins with a density of less than about 0.89 gram/cm$^3$ from Dow Chemical Co., USA, under the trade name AFFINITY®; and natural and synthetic rubber. The nonelastic material can include of a nonwoven material, for example a spunbond nonwoven, a carded nonwoven, a meltblown nonwoven or a nonwoven laminate, for example a spunbond-meltblown-spunbond (SMS) laminate. The fibers used to build up the nonwoven materials can be fibers of polyolefins, for example polyethylene or polypropylene, or of polyester. Moreover, the nonwoven material can be a mixture of several different types of fibers, or of fibers which include several different polymers, called copolymers. It is also possible for the nonelastic material to be a plastic film. In the preferred embodiment, therefore, at least the parts 13 of the two detachable parts 12, 13, of which the front side panels 10 consist, are in turn made up of at least two parts. For the sake of simplicity, however, the parts 13 are shown as single material pieces in the figures. The material of the side panels can also be air-permeable in order to increase comfort.

The aim of the elastic side panels is to give the diaper pants a good fit. It should be noted that the side panels are of course dimensioned to give the elastic force necessary, but not more. It is therefore conceivable that the side panels also have parts of nonelastic material at locations other than at the securing elements.

As material for the side panels, it is also conceivable to use two nonwoven sheets between which elastic material, elastic bands or elastic threads are secured in the stretched state. With such a material, the elastic and nonelastic parts of the side panels consist of portions with and without such elastic material.

To improve access to the detachable and resealable connections 14, the parts 13 of the front side panels 10 can have a considerably greater extent in the circumferential direction than the parts 12 cooperating with them. In this way, the connections 14 will be situated on the front of the diaper pants, which makes them easier to get access to for a parent who wishes to open or take off the diaper pants from an infant lying on his/her back. In the embodiment shown in FIG. 3, the parts 12 which have a small extent in the circumferential direction are advantageously made entirely of nonelastic material, for example a nonwoven.

It is of course also possible for the parts 13 to have a small extent in the circumferential direction instead of the parts 12, in which case the connections 14 will be close to the side seams 17, 18. In such a design, the connections are situated on the user's side and are thus more difficult to handle. However, such a design provides slightly better comfort for the wearer and reduces the risk of chafing. It is also possible to arrange the detachable and resealable connections in the rear side panels instead of in the front ones.

As will be seen from FIG. 3, the unit 7 also comprises leg elastic comprising one or more elastic threads which are arranged between the cover sheets 2 and 3 and are secured to these, in the stretched state, on both sides of the absorption body 1.

The liquid-permeable cover sheet 2 can be, for example, a nonwoven of spunbond polypropylene. Other materials which are used for liquid-permeable cover sheets, so-called top sheets, of absorbent articles, such as nonwovens of synthetic and/or natural fibers, perforated plastic sheets or laminates of such materials, can of course also be used as cover sheet 2.

The liquid-tight outer cover sheet 3 can be a plastic sheet, preferably of the breathable type, or a laminate of a plastic sheet and a nonwoven. All materials used as so-called backing sheets for absorbent articles can be used.

The absorption body 1 preferably comprises a layer of cellulose fibers with or without admixture of superabsorbents and/or binder fibers. Other materials such as foamed material or moss can be used. The absorption body can also be made up of several layers and advantageously comprises a layer of material with high permeability, for example a wadding.

An embodiment of a method for production of diaper pants according to FIG. 3 will now be described with reference to FIGS. 1 and 2. To simplify a comparison with the diaper pants in FIG. 3, the components in FIGS. 1 and 2 have been given the same reference numbers as corresponding components of the finished diaper pants in FIG. 3. For example, the web of liquid-permeable material in FIGS. 1 and 2 has been given the same reference number as the cover sheet 2 of the finished diaper pants.

The diaper pants according to FIG. 3 can be produced in the following way.

Absorption bodies 1 are placed on a running material web 2 of liquid-permeable material with the aid of a transfer wheel 19 on which absorption bodies 1 formed in a mat former wheel (not shown) have been deposited. If the absorption bodies 1 can be formed in synchrony with the advance of the material web 2, the transfer wheel can be omitted and the wheel 19 can be a mat former wheel.

A material web 3 of liquid-tight material is then placed on top of the row of absorption bodies 1. The material web 3 passes a gluing unit 20 immediately before application and is secured, with the aid of a pair of rollers 21, to the material web 2 in parts lying outside the absorption bodies 1. If appropriate, the material web 3 is also secured to the rear side of each absorption body 1. Elastic threads or elastic bands 22 are inserted with the aid of a feed unit (not shown) between the webs 2 and 3 and are secured to these with the aid of the pair of rollers 21. Transverse elastic elements, waist elastic, are also expediently applied between the webs 2 and 3 before these pass through the pair of rollers 21. For the sake of clarity, this elastic is not shown in the figures. It should be noted that the production stages described above are conventional and well known to the skilled person.

Figure 4:
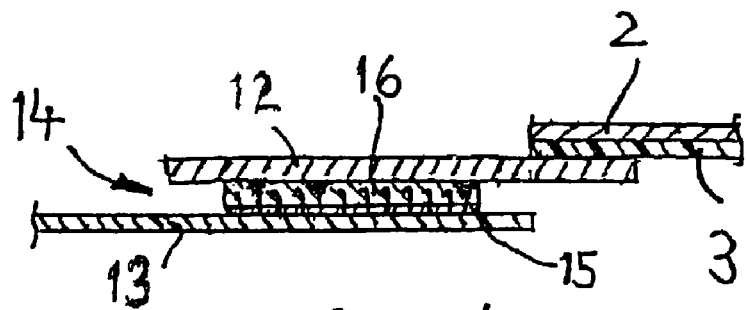
FIG. 4 shows a cross-sectional view along the line IV-IV in FIG. 3, FIGS. 5 and 6 show views, similar to FIGS. 1 and 2, of an arrangement according to a second embodiment of the invention.

The combined web 1, 2, 3 of continuous diaper pants blanks then runs through a first unit 22 in which front side panels 10 are applied to the front portion of each diaper pants blank. Each front side panel 10 has two parts 12, 13 which are connected to each other by a connection 14 (not shown in FIGS. 1 and 2) which is described with reference to FIGS. 3 and 4. The unit 22 can be arranged in such a way that, on both sides of the web of continuous diaper pants blanks, it can deliver and then secure rectangular front side panels 10 from a store of these, or the unit can also be arranged to separate rectangular side panels from a storage roller and then deliver these and secure them to the web of continuous diaper pants blanks. The side panels are attached by adhesive bonding or welding, and the unit 22 thus also comprises, in the case of adhesive bonding, a gluing unit and a stamp or the like and, in the case of welding, a welding device, for example an ultrasonic welding device. In FIG. 1, front side panels 10 are transferred from a roller 23 to a counter-roller 24 and past an ultrasonic welding device 25 in which the front side panels 10 are firmly welded in the cover sheets 2, 3. If appropriate, the welding device can also be arranged to secure the cover sheets 2, 3 to each other in parts lying outside the absorption bodies 1, in which case the gluing unit 20 can be omitted.

The web of continuous diaper pants blanks then runs past a unit 26 in which rear side panels 11 are applied to the rear portion of each diaper pants blank. The unit 26 is designed in the same way as the unit 22.

It is of course possible to apply the side panels 10 and 11 in the reverse order by switching the positions of the units 22 and 26 in the processing line.

After application of the side panels, the web of continuous diaper pants blanks runs through a cutter device 27 in which leg cutouts are formed and then through a blade roller 28 in which the web is divided up into individual diaper pants blanks. In the illustrated embodiment of the diaper pants according to the invention, part of the leg openings is included in the side panels 8, 9. It is of course possible to cut out the leg openings in the web of continuous diaper pants blanks before the application of side panels, especially if the diaper pants are designed such that that part of the side panels included in the leg openings can be straight. Instead of rectangular side panels, it is of course also possible to apply side panels which have leg recesses. However, this is not as preferred because it can considerably increase the precision requirements for application of the side panels. The leg recesses are therefore preferably cut out after the side panels have been secured to the web of continuous diaper pants blanks. In the embodiment shown, cutting of the leg recesses and of the individual diaper pants blanks takes place in two separate stages, but it is possible to use the same blade roller for cutting leg openings and for dividing the web of continuous diaper pants blanks into individual diaper pants blanks.

After the division of the web of continuous diaper pants blanks, the individual diaper pants blanks are fed to a folding device 29 via a guide arrangement (not shown), for example a guide rail and a suction conveyor. In the embodiment shown, the device 29 comprises a pair of rollers 30 and a member 31 which executes a reciprocating movement and which drives the crotch portion of the diaper pants blank into the nip 30 of the roller pair when the diaper pants blank is situated at the nip. In this way, the diaper pants blank is folded double so that the front edge is situated level with the rear edge.

After leaving the folding device 29, the double-folded diaper pants blank runs past an ultrasonic welding device 31 including an ultrasound horn 32 and a counter-roller 33, in which the edges of the front and rear side panels folded against each other are joined together.

The finished diaper pants are then fed to a packaging device (not shown).

FIGS. 5 and 6 show a second embodiment of an arrangement for production of diaper pants, which arrangement differs from the arrangement shown in FIGS. 1 and 2 mainly in that the front and rear side panels 10', 11' of two adjacent diaper pants blanks are arranged in one piece in the processing line and are divided upon division of the web of continuous diaper pants blanks. The components in the arrangement shown in FIGS. 5 and 6 which are similar to corresponding components in the arrangement in FIGS. 1 and 2 have been given the same reference numbers, with addition of a prime marker.

A precondition for being able to arrange the front and rear side panels 10', 11' of two adjacent diaper pants blanks in one piece is that the front and rear portions of adjacent diaper pants blanks are directed toward each other. For this purpose, the moulds of the mat former wheel can be expediently designed such that the absorption bodies leaving the mat former wheel have front ends and rear ends directed toward each other. If this is not the case, the transfer from the mat former wheel takes place in such a way that every second absorption body is turned 180° before the absorption bodies are placed on the transfer wheel 19. The absorption bodies 1' are then placed on the material web 2' in a row with front portions and rear portions of adjacent absorption bodies directed toward each other. A consequence of the front and rear portions of the diaper pants blanks being directed toward each other is that, after leaving the folding device 29', front and rear portions will alternately be situated uppermost in the double-folded diaper pants blank. Otherwise, the arrangement shown in FIGS. 5 and 6 functions in the same way as the arrangement shown in FIGS. 1 and 2.

In the embodiments described, the web 3, 3' of liquid-tight material is placed on top of the web 2, 2' of liquid-permeable material after the absorption bodies have been placed thereon. It is of course possible to switch the webs around so that absorption bodies are placed on the web of liquid-tight material, and the web of liquid-permeable material is applied last.

In the embodiments described, the side panels have the same extent in the lateral direction, which means that their side edges lie level with each other after the diaper pants blanks have been folded about a transverse axis. It is of course possible to give the side panels different extents in the lateral direction and to fold the side panel with the greatest lateral extent in across the other panel so that the edges of the side panels overlap each other before the panels are secured to each other.

By virtue of the fact that the detachable and resealably connected two-part side panels are applied to the web of continuous diaper pants blanks in the sealed state, the precision requirements when arranging the side panels on the web of continuous diaper pants blanks are reduced compared to the situation where the parts including the male and female elements of the seal are to be applied individually, because a deviation from the desired position of the side panels, for example in the longitudinal direction, does not entail an offset of the mutual positions of the parts included in the resealable connection. In the event of such a deviation of a side panel whose free end contains a male element which is intended to interact with a female element secured to the outer cover of the diaper pants, the male and female elements of the securing arrangement will be offset in relation to each other. This means that the resistance to opening of the connection is less than intended, the diaper pants have a less attractive appearance, and the fit after opening and resealing is not as good as intended, if one assumes that the male and female elements after opening are joined together so that they completely overlap each other. In this method, therefore, greater deviations in the longitudinal direction upon application of the side panels can be tolerated than in previously known methods.

The arrangement of the diaper pants blanks so that the front and rear portions of adjacent diaper pants blanks are directed toward each other also means that two side panels can be arranged in one piece and then divided by a straight cut in connection with the cutting of individual diaper pants blanks. This can ensure that the waist edges of the side panels and the part of the diaper pants containing the absorption body are always at the same level, which can be difficult to achieve upon application of individual side panels. It should be noted that in a web of continuous diaper pants blanks in which the front portions are directed in the same sense so that the front portion of one diaper pants blank is directed toward the rear portion of the nearest leading diaper pants blank, very great precision is needed when dividing the web into individual diaper pants blanks by means of straight cuts, so as to ensure that part of the rear portion does not end up in the front portion, or part of the front portion end up in the rear portion. If the front and rear portions have the same width and the same material composition, this has no great effect, but, if these portions have a different width or different material composition, it is of course preferred to ensure that the cut is made in exactly the right place. In the method described with reference to FIGS. 1 and 2, the front and rear side panels of adjacent diaper pants blanks are placed at a slight distance from each other so that the continuous diaper pants blank can be divided without any risk of part of the front and rear side panels being included in the wrong diaper pants blank after division of the web. The consequence of this is that the inner and outer cover sheets extend slightly beyond the side panels of the diaper pants produced by means of the method described in FIGS. 1 and 2. By means of the method described with reference to FIGS. 5 and 6, the division of the side panels takes place simultaneously with the division of the web of diaper pants blanks. The tolerances for the positioning of the side panels are thereby increased, and at the same time the position of the dividing cuts requires less precision compared to methods in which a separate side panel for each front portion is applied.

In addition, the childproof connection can be made with great care and precision since this is done in a production step before the actual diaper production. It is thus possible to use optimum web speeds, which can be considerably slower than the web speeds normally pertaining in process lines for diaper production. A number of parallel side panel blanks can be produced simultaneously if the web width is great enough. In this way, a large number of side panels can be prefabricated per unit of time without the web speed being too high.

The described method can of course be modified within the scope of the invention. For example, the side panels 10, 11 can be applied to the material web 2 before the material web 3 is applied, so that the side panels are arranged between the material webs 2 and 3 and are secured to both of these webs. The side panels can also be secured to the liquid-permeable inner cover sheet. The absorption bodies 1 can be completed with further layers, such layers being applied on top of the bodies 1 by means of further transfer or mat former wheels being added to the arrangement shown in FIGS. 1 and 2. Moreover, members for providing liquid barriers, so-called standing gathers, can be added to the arrangement. The absorption bodies can have a shape other than that shown, for example they can be rectangular or T-shaped. Types of securing elements other than velcro members can be used, for example different types of snap-fit connections, which can also be made childproof. The components included in the arrangement described are of a type generally used in production of diapers, diaper pants and similar articles and can be replaced by other components with the same function, for example the blade roller can be replaced with a punch device. The invention is therefore limited only by the content of the attached patent claims.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. A method for production of disposable diaper pants or of a sanitary panty of the disposable type with openable and resealable side panels, the method comprising:

applying a row of absorption bodies on a first continuous web of inner or outer cover sheet material;

applying a second continuous web of outer or inner cover sheet material to the first continuous web and securing the second continuous web to the first web in parts of the first continuous web lying outside the absorption bodies in order to form a web of interconnected diaper pants blanks, each of the diaper pants blanks having a front portion and a rear portion and an intermediate crotch portion;

forming a pair of first side panels, wherein each of the first side panels is formed by connecting two parts to each other with a hooks and loops fastener, wherein hooks on one part of the first side panels are welded to loops on another part of the first side panels;

after forming the pair of first side panels by connecting the two parts to each other with the welded hooks and loops fasteners, securing the pair of first side panels to respective side portions of the front portions or rear portions of the diaper pants blanks;

securing second side panels to the side portions of those of the front portions or rear portions of the diaper pants blanks which are not provided with or are intended to be provided with the first side panels;

thereafter cutting individual diaper pants blanks provided with side panels from the web of interconnected diaper pants blanks;

folding each diaper pants blank about a transverse axis in the crotch portion so that the front and rear portions of the blank lie against each other; and thereafter securing the first and second side panels of each diaper pants blank which have been folded toward other to each other.

2. The method according to claim 1, wherein in the web of interconnected diaper pants blanks the absorption bodies are arranged such that front and rear portions of the absorption bodies are directed towards each other in adjacent absorption bodies in the row of absorption bodies so that the front portion of one of the absorption bodies is adjacent the rear portion of an adjacent absorption body, and in that the first and second side panels of adjacent diaper pants blanks extend across both the mutually adjacent front and rear portions.

3. The method according to claim 1, wherein the first and second side panels are secured to the outer or inner cover sheet of the diaper pants blanks.

4. The method according to claim 1, wherein the first and second side panels are placed between the outer and inner cover sheets and secured to both the inner cover sheet and the outer cover sheet.

5. The method according to claim 1, wherein the side panels at least partially comprise elastic material.

6. The method according to claim 1, wherein the two parts of each first side panel comprises a childproof connection.

7. A method for production of disposable diaper pants or of a sanitary panty of the disposable type with openable and resealable side panels, the method comprising:

applying a row of absorption bodies on a first continuous web of inner or outer cover sheet material;

applying a second continuous web of outer or inner cover sheet material to the first continuous web and securing the second continuous web to the first continuous web in parts of the first continuous web lying outside the absorption bodies in order to form a web of interconnected diaper pants blanks, each of the diaper pants blanks having a front portion and a rear portion and an intermediate crotch portion;

securing first separate side panels to side portions of the front portions or rear portions of the diaper pants blanks, each of the first separate side panels comprising two parts connected to each other by a hooks and loops fastener, wherein hooks on one part of the first side panels are welded to loops on another part of the first side panels;

securing second separate side panels to the side portions of those of the front portions or rear portions of the diaper pants blanks which are not provided with or are intended to be provided with first side panels; and thereafter cutting individual diaper pants blanks provided with side panels from the web of interconnected diaper pants blanks;

folding each diaper pants blank about a transverse axis in the crotch portion so that the front and rear portions of the blank lie against each other; and thereafter securing the first and second side panels of each diaper pants blank which have been folded toward other to each other.

8. The method according to claim 1, wherein the first and second continuous webs move in a machine direction, and the absorption bodies extend with their greatest dimension extending in the machine direction.

9. The method according to claim 1, wherein the first and second continuous webs move in a machine direction, and the side panels are connected to the front and rear portions of the diaper blanks with respective connection seams that extend in the machine direction.

* * * * *